Feb. 23, 1965 R. S. MOORE Plant Pat. 2,483
MINIATURE ROSE PLANT
Filed Nov. 5, 1963
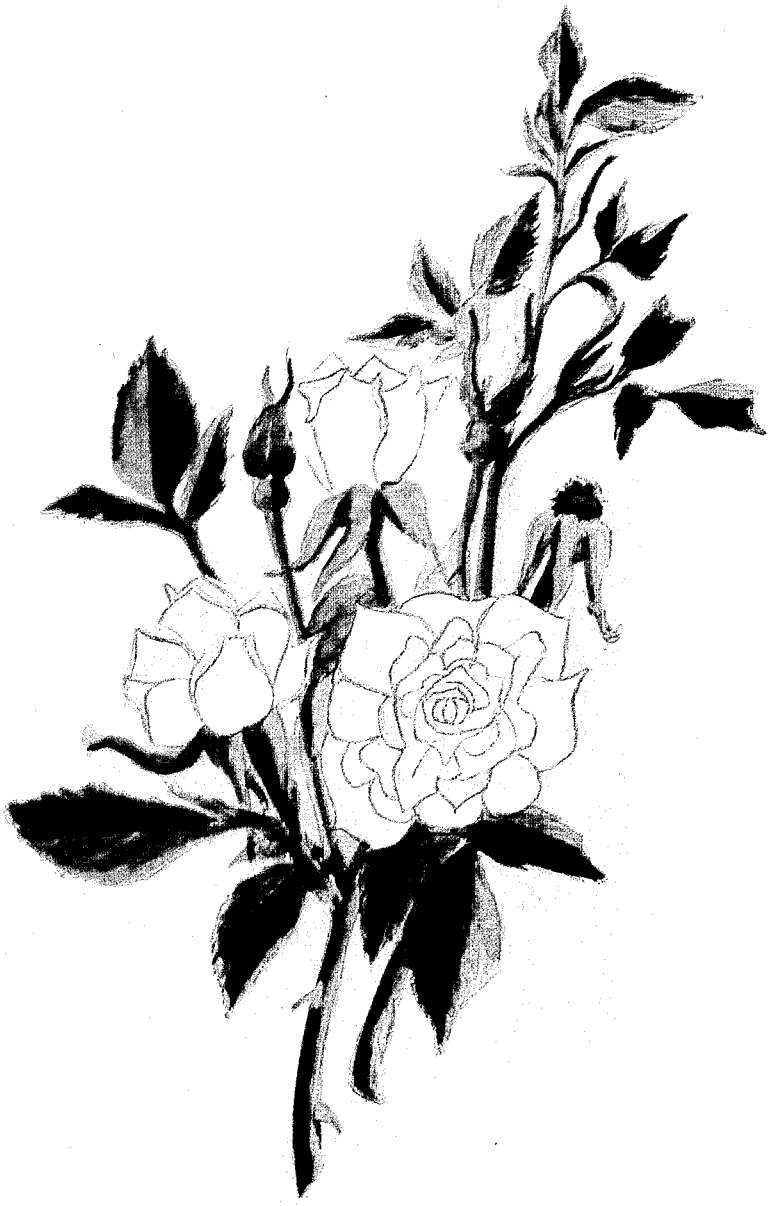
WITNESS
Jeanette Nunn Copley
INVENTOR
Ralph S. Moore
ATTORNEYS United States Patent Office Plant Pat. 2,483
Patented Feb. 23, 1965

2,483
MINIATURE ROSE PLANT

Ralph S. Moore, 2519 E. Mineral King, Visalia, Calif.

Filed Nov. 5, 1963, Ser. No. 321,706
1 Claim. (Cl. Plt.—9)

The present invention relates to a new and distinct variety of hardy, dwarf, bush type rose plant of the hybrid miniature class; the variety being primarily characterized—as to novelty—by bright yet soft pink bi-color flowers which in general color effect are pink with a softer pink reverse.

The variety is further characterized by:

An abundance of bloom, with flowers borne singly or several to stem in loose clusters.

A sweet fragrance.

A plant which is vigorous, of rounded upright shape, and with glossy, medium-small foliage; the flowers and foliage being similar in size to the variety Dian (United States Plant Patent No. 1,808). The plant which has a normal average height of 12" to 16" at maturity can be easily maintained at 10" to 12" by occasional trimming.

A plant which grows and blooms satisfactorily both in the greenhouse and outdoors; is a good potted plant; and provides excellent garden decoration as well as cut flowers.

The present variety of miniature rose was originated by me in my nursery located at Visalia, California, under conditions of careful control and observation, as a cross between an unnamed and unpatented seedling (*Rosa wichuraiana* × Floradora, both unpatented) as the seed parent, and Little Buckaroo (United States Plant Patent No. 1,726) as the pollen parent.

Subsequent to origination of the variety I successfully asexually reproduced it, in my nursery located as aforesaid, by budding as well as cuttings; the reproductions have run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy, dwarf; bush; seedling; greenhouse; outdoors; cut flowers; garden decoration; potted plant.

Class: Hybrid miniature.

Flowers:

*Continuity.*—Continuous.

*Fragrance.*—Sweet; moderate.

Flowers borne: Usually several to stem in loose clusters on normal strength medium length stems (sometimes singly).

Quantity of bloom: Abundant both outside and in greenhouse.

Bud:

*Peduncle.*—Medium length; slender; erect; light green; numerous reddish thorns (sometimes nearly smooth).

*Before calyx breaks.*—Size—small. Form long; pointed; usually without foliaceous appendages on surface of the bud; with foliaceous parts extending beyond the tip of the bud equal to one-fourth or more of its length. Color—medium green.

*As calyx breaks.*—Color—pink; shows a little white at base.

*As first petal opens.*—Size—small. Form short; pointed. Color: outside—Tyrian Rose 24/1—white at base; inside—Tyrian Rose 24—white to light yellow at base.

*Opening.*—Usually opens well; petals may burn some in hot dry weather.

Bloom:

*Size when fully open.*—Small, averaging 1½".

*Petalage.*—Very double—from 50 to 60 petals, arranged regularly.

*Form.*—Cupped and full at first, with petals rolled loosely outward, and later at maturity being loosely rolled outward, often with numerous short narrow petals tightly rolled inward around the pistils.

Petals: Fairly thick; soft; satiny both inside and outside.

*Shape.*—Outside petals oval (broad lanceolate); intermediate—broad lanceolate; inside lanceolate.

*Color.*—Newly opened flower from a plant grown outdoors (May 1963), Visalia California. Outside petal: outside surface—Fuchsine Pink 627/3, shading to white or near-white at base; inside surface—Fuchsine Pink 627/2, shading to near white at base. Intermediate petal: outside surface—Fuchsine Pink 627/3 with a bit of yellow at base; inside surface—Fuchsine Pink 627/2, with a bit of yellow at base. Inner petal: outside surface—Tyrian Rose 24/1 shading to near white at base; inside surface—Tyrian Rose 24/1 shading to near white with a bit of yellow at base.

*General color effect.*—Newly opened flower—fresh bright pink. Three days open—softer pink.

*Behaviour.*—Petals often persist for a time. Petals may burn some in hot dry weather.

*Flower longevity (May 1963).*—Bush in garden—3 to 4 days. Cut flowers kept at living room temperature—2 to 3 days.

Reproductive organs:

*Stamens.*—Very few to none; arranged irregularly about pistils; mixed with petaloids.

*Filaments.*—Short; yellow.

*Anthers.*—Small; yellow; variable in opening.

*Pollen.*—Very scarce.

*Pistils.*—Few.

*Styles.*—Uneven; medium length; bunched.

*Stigma.*—White.

*Ovaries.*—All enclosed in calyx.

*Hips.*—None.

*Sepals.*—Permanent; spear shaped; recurved.

*Seeds.*—None.

Foliage:

*Leaves.*—Compound of five leaflets; abundant; moderately small; leathery; very glossy.

*Leaflets.*—Shape—lanceolate; apex acute; base round. Margin—serrate. Color—normal green; new growth sometimes tinted bronze. Rachis—medium strength; upper side smooth, grooved with a few light hairs; under side sparsely thorny. Stipules—medium length; narrow; short length points, turning out at an angle of more than 45 degrees.

Growth:

*Habit.*—Dwarf; bushy; upright; much branched.

*Growth.*—Free; vigorous.

*Canes.*—Medium.

*Main stems.*—Color—dull green. Thorns—moderately thorny; short; medium length; hooked downward; color—gray or gray-brown. Prickles—none. Hairs—none.

*Branches.*—Color—bright green. Thorns—moderately thorny; short; hooked downward; short oval base. Prickles—none. Hairs—none.

*New shoots.*—Color—bright green, often tinted bronze. Thorns—moderately thorny; short; hooked downward; base short, oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, dwarf, upright, much branched, bush type, as illustrated and described, characterized by buds and flowers resembling the Dian miniature rose in general form but being slightly larger when fully open, the buds somewhat more pointed, and the color more pink than red; the flowers being softly bicolor in that the top surface of petals is generally deeper pink that the lower surface, with the general color effect being a soft but bright pink; and further characterized by a plant which is vigorous in growth, easy to propagate from cuttings, with medium-small glossy foliage and an abundance of bloom, with the flowers borne singly or several to stem in loose clusters.

No references cited.

ABRAHAM G. STONE, *Primary Examiner.*